United States Patent [19]

Chaudhuri et al.

[11] Patent Number: 5,229,355
[45] Date of Patent: Jul. 20, 1993

[54] LEACHING INHIBITION OF CROP TREATING CHEMICALS WITH POLYMERS

[75] Inventors: Ratan K. Chaudhuri, Butler; Kolazi S. Narayanan, Palisades Park, both of N.J.

[73] Assignee: ISP Investments Inc., Wilmington, Del.

[21] Appl. No.: 843,025

[22] Filed: Feb. 28, 1992

[51] Int. Cl.$^5$ .................... A01N 25/10; A01N 25/22; A01N 25/24; A01N 43/70
[52] U.S. Cl. ................................ 504/113; 504/232; 504/324; 504/342; 71/DIG. 1
[58] Field of Search ............. 71/93, 115, 118, DIG. 1; 504/113

[56] References Cited

U.S. PATENT DOCUMENTS 3,886,125  5/1975  Chromecek ................. 71/DIG. 1
4,129,435  12/1978  Takematsu et al. ............... 71/93
5,022,917  6/1991  Allan ........................ 71/DIG. 1

Primary Examiner—Glennon H. Hollrah
Assistant Examiner—S. Mark Clardy
Attorney, Agent, or Firm—Marilyn J. Maue; Joshua J. Ward

[57] ABSTRACT

This invention relates to inhibiting leaching of crop treating chemicals into the ground water, aqua-system and surrounding soil of the treatment site by contacting the plant or plant site with an effective leach inhibiting, plant tolerating amount of a copolymer of a maleic acid, the corresponding $C_1$ to $C_6$ alkyl ester of said acid or a mixture thereof and a comonomer of an alkyl alpha alkenyl ether; which copolymers have a molecular weight (Mw) of from about 8,000 to about 3,000,000 and can be directly incorporated into a standard agrichemical formulation.

15 Claims, No Drawings

LEACHING INHIBITION OF CROP TREATING CHEMICALS WITH POLYMERS

In one aspect, this invention relates to a polymeric material which is readily incorporated into an agrichemical formulation in order to inhibit leaching of the active agrichemical into the ground water and surrounding area of treatment. In another aspect the invention relates to the use of a composition for more efficient use of the active agrichemical in reduced amounts.

BACKGROUND OF THE INVENTION

Agrichemical contamination is a growing concern since more than 12 different pesticides have been found in the ground water in at least 25 states in this country alone. Studies have shown that pesticide residues in ground water are increasing and are particularly severe where agronomic and horticultural crops are grown in permeable sandy soils or in locations which receive heavy rainfall. Among the chemicals which are particularly troublesome are herbicides such as bromacil, atrazine, metribuzin, dicamba and metolachlor, nematicides such as aldicarb, fungicides such as triforine, pencanazole and bendiocarb and insecticides such as diazinone, chloropyrophor, and ethion, which have been found in drinking water. Hence, there is an acute need to restrict the downward movement of pesticides, herbicides, fungicides and other organic pollutants in the soil without reducing their agricultural efficacy.

Control of agrichemical leaching is a complex art which depends on many factors including rainfall, soil acidity and type, as well as plant tolerance. Various solutions to the problem have been proposed including controlled release formulations and encapsulated suspensions of the harmful active chemical. Surfactants have been employed for restricting the downward movement of urea herbicides such as diuron, linuron and monuron (see Weeds, by D. E. Bayer, Vol. 15, pages 249-252, 1967). The mobility of metribuzin in the soil has been reduced by the use of polyvinyl alcohol polymers, as discussed by C. L. McCormick and M. M. Fooladi, 1980 (Controlled Activity Polymers with Labile Bonds to Pendent Metribuzin in Controlled Release of Bioactive Materials, R. Baker, Academic Press, New York, pages 317-330). However, it was found that metribuzin formed covalent linkages with the polyvinyl alcohols which resulted in hindering release from the alcoholic polymer for plant uptake. Certain pine craft lignins have shown some decrease in the leaching losses of atrazine and 2,4-D (see Weed Science, E. P. Dunigan and T. Macintosh, 1971, Volume 29 pages 279-282 and Controlled Release Technologies: Methods, Theory and Application by H. T. Dellicolli, 1980, Volume II, C.R.C. Press, Boca Raton, Fla., pages 225-234). Several other leaching inhibitors have been proposed; however, the chemicals currently used to inhibit downward movement have been found to be highly specific to certain chemical types and do not extend generally to plant treating agrichemicals of different chemical classes.

Accordingly, it is an object of this invention to provide a leach inhibiting chemical which is more broadly effective in preventing or inhibiting downward movement of various plant treating materials.

Another object of this invention is to provide an economically produced chemical which prevents or minimizes the movement of toxic chemicals in the soil and retains the plant treating agent in the root or immediate surrounding area of the soil where it is applied and where it is most effective.

Another object of this invention is to provide a leach inhibiting chemical which permits more efficient use of a crop treating agent in reduced amount and which prevents or minimizes contamination of the aquasystem.

These and other objects of the invention will become apparent to one skilled in the art from the following description and disclosure.

THE INVENTION

In accordance with this invention, there is provided a leach inhibiting, copolymer which is readily combined with an agrichemical or incorporated into an agrichemical formulation. The leach inhibiting copolymers of this invention are copolymers, preferably water insoluble copolymers having less than 10% water solubility, such as copolymers of maleic acid, a $C_1$ to $C_6$ mono- or diester of said acid or a mixture thereof and a $C_2$ to $C_{25}$ comonomer of an alkyl alpha alkenyl ether or an alpha olefin, which copolymer has a molecular weight (Mw) of between about 8,000 and about 3,000,000. The structure of said copolymer is defined by the formula

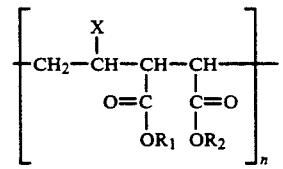

wherein X is $C_1$ to $C_{25}$ alkyl, alkoxy, aryl, aryloxy; $R_1$ and $R_2$ are each independently hydrogen or $C_1$ to $C_6$ alkyl and n has a value of from 25 to 5000.

Examples of suitable maleate esters include mono-and di- methyl, ethyl, propyl, isopropyl, butyl, t-butyl, hexyl, cyclohexyl and dimethylpropyl esters of maleic acid or mixtures thereof. The polymer may also contain mixtures of maleic acid and at least one of the ester derivatives as the monomeric portion of the polymer.

Representative examples of the alkyl alpha-alkenyl ether comonomer include vinyl methyl ether, vinyl ethyl ether, vinyl propyl ether, vinyl isopropyl ether, vinyl pentyl ether, vinyl butyl ether, vinyl isobutyl ether, vinyl t-butyl ether, vinyl hexyl ether, vinyl methylbutyl ethers, 2-ethenyl butyl ether, 2-ethenyl propyl ether, 2-ethenyl ethyl ether, 2-ethenyl hexyl ether, 2-ethenyl dodecyl ether, 2-ethenyl benzyl ether, vinyl ethylbutyl ethers and mixtures thereof.

Illustrative of the comonomeric alpha olefins are ethene, propene, 1-butene, 1-octene, 1-hexadecene, 1-eicosene, 1-pentacosene, etc. and mixtures of any of the above comonomers.

The preferred polymers of this invention are the copolymers of maleic acid or the $C_1$ to $C_4$ half esters of maleic acid with a methyl, ethyl or butyl vinyl ether having a molecular weight of between about 10,000 and about 1,000,000 and the most preferred copolymers are shown in following Table A.

TABLE A

| Polymer | Mn | Mw | $N^*_{sp}$ |
|---|---|---|---|
| (1) Poly[methylvinyl ether/ maleic acid] copolymer (Gantrez ® S-95 or S-97) | 3000–500,000 | 10,000–3,000,000 | 0.2–15 |
| (2) Monobutyl ester of | 3000–500,000 | 10,000– | 0.2–15 |

TABLE A-continued

| Polymer | Mn | Mw | N*$_{sp}$ |
|---|---|---|---|
| poly (methylvinyl ether/maleic acid) Gantrez ® ES-425 | | 3,000,000 | |
| (3) Mono isopropyl ester of poly (methylvinyl ether/maleic acid) Gantrez ® ES-335 | 3000–500,000 | 10,000–3,000,000 | 0.2–15 |
| (4) Poly[butyl vinyl ether/maleic acid] copolymer Butyl analyse of Gantrez ® S-95 | 3000–500,000 | 10,000–3,000,000 | 0.2–15 |

Specific Viscosity $(N_{sp}) = \frac{N \text{ solution} - N \text{ solvent}}{N \text{ solvent}}$
for 1% solution, in water or denatured alcohol.

The above polymer/agrichemical is contacted with the plant or surrounding soil area in a pre-emergent or post-emergent application and in an effective leach inhibiting, plant tolerating amount. In combining with the active agrichemical, as little as 0.001 weight % of instant polymer, based on the total composition, is effective to inhibit leaching with various agrichemicals. However a weight ratio of agrichemical to polymer of between about 0.1:1 and about 10:1 is recommended and between about 0.3:1 and about 2:1 is preferred.

Of the present polymeric leach inhibitors, those containing between about 10 and about 90 weight % of the alkyl alkenyl ether monomer are desirable and those containing containing not more than 80 weight % of the comonomer are recommended for most plant species.

Representative crop treating agents which are commonly employed and whose mobility is controlled by the present leach inhibiting agents include a wide range of herbicides, nematocides, insecticides, fungicides, plant growth promoting or controlling chemicals and other crop treating products. These include herbicides such as Dicamba, Alachlor, Aldicarb, Amiben, Anisomycin, Arsenal, Assert, Atrazine, Bentazone, Bromacil, Bialaphos, Butylate, Carbofuran, Chloramben, Chlortoluron, Cyanazine, Banval, Cotoran, Dalapon, 2,4-D, Dicamba, Dinoseb, Diquat, Diuron, Dibromo-chloro propane, EDB, EPTC, Glyphosate, Glean, Hyvar, Linuron, Lexone, Lontrel, Monuron, Metribuzin, Mecoprop, Metolachlor, Nortron, Norflurazon, Pramitol, Prometryn, Pyramin, Rhizobitoxin, Reflex, Scepter, Simazine, Sinbar, Tordon, Tentoxin, Terbacl, Trifluralin, Ureas, Velpar, etc.; insecticides such as Azodrin, Bendiocarb, Diazinon, Dylox, Furadan, Metasystox, Mocap, Phosphamidon, Temik, Trigard, Vydate, and others cited in The Agricultural Chemicals Handbook, Second Ed., Royal Society of Chemistry (1987). Nematocides such as aldicarb and fungicides such as triforine and pencanazole are also suitably combined with the present polymer for reduced leaching. The agrichemicals which are particularly compatible and efficacious with the present leach inhibiting agents include the herbicides bromacil, atrazine, dicamba, metolachlor, diuron, assert bisulfate, simazine, diazinone, triforine and perconazide.

All of the above agrichemicals are known and appropriate plant dosages and tolerances have been described for each product. The formulated active agents containing the copolymer can be sprayed or misted to contact treating sites according to known procedures. Since the present polymers are non-toxic, their incorporation into the formulation does not alter, and in some cases may reduce, the required effective dosage of active agrichemical.

Generally the present polymer is applied as an aqueous solution containing from about 25 to about 65 wt. % copolymer; although alcoholic solutions in the same concentration may also be employed.

The inhibiting effect of the present polymer is achieved by complexing, encapsulation, or blending with the crop treating agent, and applying to the plant site. In all instances, a marked reduction, and in some cases almost complete elimination, of downward transmigration of the agrichemical is achieved. In addition to the inherent leachability of certain agrichemicals, the soil also plays an important role such that the greatest leaching is found in highly porous, low organic soils such as those found in Florida; whereas the loamy or clay soils of the midwest or northwest have lower leachability. Accordingly, the amount of polymer in the agrichemical formulation can be adjusted to overcome such problems.

The agrichemical formulations containing the present copolymers are directly prepared by simply mixing the polymer into the standard agrichemical formulation or a preformed concentrate thereof, followed by recommended dilution, under ambient conditions.

An advantage of the present leach inhibiting polymers is that they are less specialized with respect to a certain group of agrichemical treating agents. Also, the use of the present compounds affords more efficient use of the agrichemical since the later is retained on the plant or in the vicinity of the root system. Thus, in many cases, smaller amounts of the agrichemical is required for the desired affect. Another advantage is that the present polymers do not alter the dispersion properties of the agrichemical formulation and in some cases may actually enhance sprayability. In addition to the plant treating chemical the agrichemical formulations may also include an inert diluent such as petroleum distillate, mineral oil, ethylene glycol, or water to regulate dosage.

Various surfactants, such as lignin sulfonate, naphthalene/formaldehyde condensate sulfonate, alkoxylated phenols, and the like can also be added in amounts up to about 5 wt. % of the total composition to increase agrichemical solubility. Other adjuvants such as emulsifiers, suspension aids and preservatives, can also be included in the formulation if desired. The leach inhibiting formulation can also be applied as a powder for crop dusting; in which case the formulation is dried to a particulate solid before use.

A further advantage of the present polymers is that they are non-toxic and are environmentally safe; thus they do not add to soil contamination. Additionally the present polymers may increase the organic content of the soil, thus benefiting future crops. These and many other benefits will be realized by the use of the present polymeric compounds.

Having thus generally described the invention, reference is now had to the accompanying examples which illustrate specific and preferred embodiments, but which should not be construed as limiting to the scope of the invention as more broadly described above and in the appended claims.

EXAMPLES I–IX

The following polymers 1–4 were mixed with Agrichemicals A-C.
Polymers

1. GANTREZ® S-95 solid (5% aqueous solution having a pH of about 2).
2. GANTREZ® ES-425 as a 50% ethanol solution.
3. GANTREZ® ES-335 as a 50% isopropanol solution.
4. Poly(butyl vinyl ether/maleic acid monomers) (5% aqueous solution having a pH of about 3), a weight average molecular weight of 50,000–75,000 and a polydispersity of 2–3.

AGRICHEMICALS
A. Dicamba
B. Atrazine
C. Metolachlor

The above mixtures were prepared by procedure X or Y.

X. The agrichemical (15 g.) and the polymer (15 g.) were dissolved in a common solvent and mixed at 55° C. for 4 hours; after which the solvent used for solubilizing was stripped off under reduced pressure and the solid polymer/agrichemical product (20–30 g.) was dried and recovered.

Y. The same as procedure X, except that, where the product is an amorphous gel, it was dissolved in a solvent and the final product is a liquid.

The coprecipitated or complexed products of polymers 1–3 are reported in following Table I.

TABLE B

| CHEMICAL PROPERTIES OF HERBICIDES | | | | |
|---|---|---|---|---|
| Herbicide | Chemical Nature | Solubility (mg/L) | Half Life (d) | $K_{oc}$ | Leaching Potential+ |
| Atrazine | Basic | 33 | 60 | 100 | 17 |
| Dicamba | Acidic | 400,000* | 14 | 2 | 1.4 |
| Metolachlor | Nonionic | 530 | 90 | 200 | 22 |

+Leaching Potential is $K_{oc}$/half life $\times$ 10. The leaching potential varies inversely with the number value
*as dimethyl ammonium salt

TABLE I

| Example No. | Agrichemical | Polymer | Initial Agrichemical wt. ratio | Prep. Method | Solubilizing Agent | State of Final Product/Solvent | Assay* |
|---|---|---|---|---|---|---|---|
| I | A | 1 | 1:1 | X | MeOH | solid/none | 51 |
| II | A | 2 | 1:1 | Y | EtOH | liquid/EtOH | 10.8 |
| III | A | 3 | 1:1 | X | EtOH | solid/none | 52.2 |
| IV | B | 1 | 1:1 | X | EtOH THF 50:50 | solid/none | 46.7 |
| V | B | 2 | 1:1 | X | EtOH THF 50:50 | solid/none | 50.8 |
| VI | B | 3 | 1:1 | X | EtOH THF 50:50 | solid/none | 50.2 |
| VII | C | 1 | 1:1 | X | MeOH | solid/none | 51.8 |
| VIII | C | 2 | 1:1 | Y | EtOH | liquid/EtOH | 9.3 |
| IX | C | 3 | 1:1 | Y | EtOH | liquid/EtOH | 13.9 |

*by UV analysis, % Agrichemical

EXAMPLES X–XVIII

The above polymer/agrichemicals were each targeted with 8500 cpm* of the corresponding radioactive $^{14}$C doctored agrichemical and then introduced at a rate of 5 lbs/acre into the top of an open bottom plexiglass 7 cm diameter, 8 cm long column containing 450 g of Polk County Florida surface soil. Then, water at room temperature was added in 4 increments of 125 ml. each to simulate 4 pore volumes i.e. normal rain conditions. The $^{14}$C activity in each of the effluent solutions was assayed and the relative % of agrichemical recovered compared to 100% recovery in the absence of the present polymer is reported in the following Table II.

* curie/million

TABLE II

| | | % Agrichem in Effluent | | | | |
|---|---|---|---|---|---|---|
| Example | Sample of Ex. | First Pore V. | Second Pore V. | Third Pore V. | Fourth Pore V. | Total |
| X | I | 1.00 | 29.7 | 21.6 | 14.4 | 65.8 |
| XI | II | 3.1 | 20.0 | 27.8 | 14.6 | 65.5 |
| XII | III | 16.8 | 64.7 | 8.1 | 7.7 | 97.3 |
| XIII | IV | 7.61 | 30.46 | 19.62 | 19.83 | 77.52 |
| XIV | V | 4.81 | 10.65 | 20.75 | 39.66 | 75.87 |
| XV | VI | 3.00 | 44.4 | 30.80 | 19.00 | 97.20 |
| XVI | VII | 9.52 | 38.47 | 29.12 | 16.64 | 93.76 |
| XVII | VIII | 7.63 | 35.01 | 19.76 | 13.17 | 75.56 |
| XVIII | IX | 11.27 | 37.26 | 22.53 | 14.12 | 85.18 |

EXAMPLES XIX–XXX

Blends of the above polymer/agrichemicals in commercial formulations containing surfactant, emulsifier and diluent were prepared as follows.

The polymer (5.0 g on 100% basis) was added to each of the following commercial agrichemical liquid formulations D-F to provide a weight ratio of 1:1 polymer to agrichemical and diluted with water to obtain a solution containing 10 wt. % of polymer and 10 wt. % agrichemical.

D. Banvel herbicide containing 40% Dicamba in 4 lbs/gal of water
E. Aatrex 4L containing 40.8% Atrazine
F. Dual containing 86.4% Metolachlor The resulting solutions or emulsions were then targeted with 8500 cpm of radioactive $^{14}$C agrichemical of the same species. The resulting mixtures were individually added to the top of a separate column similar to that above at a rate of 5 lbs. agrichemical/acre and the leachates from each of the 4 water washings were collected and analyzed.

The column employed in this study was used at bulk density of soil at packing. Each pore volume of water applied on the top of the soil column was equivalent to 3.2 cm (1.28 inch) of rainfall. The amount of herbicide leached was calculated on the basis of $^{14}$C-herbicide applied and recovered from the leachate. The difference between these two values represented that which was adsorbed by the soil.

Controls were run under exactly the same conditions with the same agrichemicals, except that the inhibiting polymer of this invention was omitted. In each control 100% leaching of agrichemical occurred. The analysis of the leachate from each of the 4 pore volumes is reported in following Table III.

TABLE III

Relative % of Agrichemical Recovered Compared To 100% Leaching with Control*

| Example | Polymer | Agri-chemical | 1st Pore | 2nd Pore | 3rd Pore | 4th Pore | Total |
|---|---|---|---|---|---|---|---|
| XIX | 1 | D | 20.2 | 43.6 | 2.8 | 1.70 | 68.30 |
| XX | 2 | D | 1.2 | 21.4 | 6.2 | 10.6 | 39.40 |
| XXI | 3 | D | 2.7 | 35.2 | 13.2 | 11.7 | 62.8 |
| XXII | 4 | D | | | | | |
| XXIII | 1 | E | 6.06 | 38.48 | 23.64 | 13.64 | 81.82 |
| XXIV | 2 | E | 4.75 | 27.27 | 32.53 | 19.19 | 83.75 |
| XXV | 3 | E | 5.15 | 26.06 | 22.83 | 24.55 | 78.59 |
| XXVI | 4 | E | | | | | |
| XXVII | 1 | F | 14.98 | 35.85 | 17.73 | 9.9 | 78.55 |
| XXVIII | 2 | F | 10.92 | 29.64 | 17.35 | 10.82 | 68.76 |
| XXIX | 3 | F | 31.37 | 19.97 | 11.14 | 12.93 | 75.41 |
| XXX | 4 | F | | | | | |

*By $^{14}C$ activity assay using Scintillation counter, % Agrichemical

EXAMPLES XXXI–XLIV

Bioassays of selected samples (i.e. products of Examples XIX to XXVIII) were made and results reported in Table IV. The procedure for these examples is as follows.

The indicated polymer/agrichemical formulation was introduced into a 130 cm × 10 cm soil packed column. In these experiments, 2.5 cm simulated rainfall was used for Dicamba 7.5 cm simulated rainfall for Atrazine and Metolachlor was employed by adding water at the rate of 1.5 cm/hr. After leaching, the columns were allowed to drain overnight and split longitudinally into two halves. Each half was planted with alfalfa or rye grass (as indicated) in 5 cm spaced rows. The % injury as a function of herbicide movement at different heights are shown in Table IV.

At every 15 cm from bottom of the column, a ridge of silicone was applied on the inside wall of each half of the column to prevent "edge flow" of water along the soil-wall interface. A PVC end-cap with a small drain hole was fitted to the bottom of the column and the columns were packed with Florida soil from respective depths to provide a Florida soil profile. Soil-packed columns were kept in upright position and the soil was saturated with water and allowed to drain overnight; after which the commercial formulation of herbicide (5 kg ai/ha) with or without polymers (5 kg/ha) was introduced to the top of the column. A 2 ml solution of each treatment was applied uniformly on the soil surface as several drops using pasteur pipet. Columns were leached by pouring distilled water over filter paper placed on the soil surface to ensure uniform distribution of water and leaching was measured at 15, 30, 45, 60 and 60+ cm depths.

TABLE IV

% Alfalfa Injury (Application rate 5 kg/ha or 4.8 lbs/acre)

| Example | Sample % % of Ex. | Column Depth (cm) | | | | | Total % Decrease |
|---|---|---|---|---|---|---|---|
| | | 0–15 | 15–30 | 30–45 | 45–60 | 60–120 | |
| XXXI | XIX | 100 | 100 | 100 | 83 | 0 | 4 |
| XXXII | XX | 100 | 100 | 92 | 21 | 0 | 22 |
| XXXIII | XXI | 100 | 100 | 100 | 75 | 0 | 6 |
| XXXIV | XXII | | | | | | |
| XXXV | Control (no polymer) | 100 | 100 | 100 | 100 | 0 | 0 |
| XXXVI | XXIII | 100 | 83 | 0 | 0 | 0 | 8 |
| XXXVII | XXIV | 100 | 66 | 0 | 0 | 0 | 17 |
| XXXVIII | XXV | 100 | 83 | 0 | 0 | 0 | 8 |
| XL | Control (no polymer) | 100 | 100 | | | | 0 |

% Rye Grass Injury (Application rate 10 kg/ha or 8.9 lbs/acre)

| Example | Sample % of Ex. | Column Depth (cm) | | | Total % Decrease |
|---|---|---|---|---|---|
| | | 0–15 | 15–30 | 30–120 | |
| XLI | XXVII | 100 | 92 | 0 | 4 |
| XLII | XXVIII | 100 | 75 | 0 | 12.5 |
| XLIII | XXX | | | | |
| XLIV | Control (no polymer) | 100 | 100 | 0 | 0 |

The above examples illustrate various embodiments and preferred leach inhibiting compositions of this invention; however, it will be understood that substitutions of the crop treating chemicals referred to in the foregoing description, or their mixtures, can be made to replace those used in the respective Examples without departing from the scope of this invention. Similarly, any of the maleic polymers set forth in the disclosure, or their mixtures, can be substituted for those employed in the above Examples, to provide leach inhibition of the agrichemical selected. From the above description, it will also become apparent that many modifications and alterations can be made in the preparations of the leach inhibiting compositions which are within the scope of this invention.

What is claimed is:

1. A leach inhibiting agrichemical composition comprising an active plant growth regulating agrichemical, an inactive carrier and a leach inhibiting amount of a copolymer of maleic acid, the corresponding $C_1$ to $C_6$ alkyl ester or mixtures thereof and a $C_2$ to $C_{25}$ comonomer of an alkyl alpha alkenyl ether or an alpha olefin; said copolymer having a Mw between about 8,000 and about 3,000,000.

2. The composition of claim 1 wherein the copolymer contains between about 10 and about 90 wt. % of comonomer.

3. The composition of claim 1 wherein the weight ratio of agrichemical to copolymer is between about 0.1:1 and about 10:1.

4. The composition of claim 3 wherein said ratio is between about 0.3:1 and about 2:1.

5. The composition of claim 1 wherein the copolymer is the copolymer of maleic acid and a comonomer selected from the group of a $C_1$ to $C_4$ alkyl vinyl ether.

6. The composition of claim 1 wherein the copolymer is the copolymer of a $C_1$ to $C_4$ alkyl ester of maleic acid and methyl vinyl ether.

7. The composition of claim 6 wherein the copolymer is the copolymer of the monobutyl ester of maleic acid and methyl vinyl ether.

8. The composition of claim 6 wherein the copolymer is the copolymer of the monoisopropyl ester of maleic acid and methyl vinyl ether.

9. The composition of claim 5 wherein the copolymer is the copolymer of maleic acid and butyl vinyl ether.

10. The composition of claim 1 wherein said carrier is water and the composition is an aqueous solution or an emulsion.

11. The composition of claim 10 wherein said carrier is an aqueous alcohol solution.

12. The composition of claim 1 wherein the Mw of the copolymer is between about 10,000 and about 1,000,000.

13. A method of inhibiting leaching of an active plant growth regulating agrichemical which comprises contacting a plant or plant site with a leach inhibiting amount of the composition of claim 1.

14. The method of claim 13 wherein said composition is applied in a dry particulate state.

15. The method of claim 13 wherein said composition is applied as an aqueous solution or emulsion.

* * * * *